(12) United States Patent
Wiznia et al.

(10) Patent No.: US 11,857,504 B1
(45) Date of Patent: Jan. 2, 2024

(54) PATIENT-CONTROLLED LIQUID ORAL MEDICINE DISPENSER AND DEACTIVATION SYSTEM

(71) Applicant: YALE UNIVERSITY, New Haven, CT (US)

(72) Inventors: Daniel Wiznia, New Haven, CT (US); Jinlei Li, New Haven, CT (US); Claudia See, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 18/328,231

(22) Filed: Jun. 2, 2023

Related U.S. Application Data

(60) Provisional application No. 63/418,182, filed on Oct. 21, 2022, provisional application No. 63/366,032, filed on Jun. 8, 2022.

(51) Int. Cl.
*A61J 7/04* (2006.01)
*A61J 7/00* (2006.01)
*A61J 1/22* (2006.01)
*G16H 20/13* (2018.01)

(52) U.S. Cl.
CPC ............... *A61J 7/0053* (2013.01); *A61J 1/22* (2013.01); *G16H 20/13* (2018.01); *A61J 2200/30* (2013.01); *A61J 2200/70* (2013.01)

(58) Field of Classification Search
CPC .......... A61J 1/22; A61J 7/0038; A61J 7/0445; A61J 2200/30; A61J 7/04
See application file for complete search history.

*Primary Examiner* — Deanna K Hall
(74) *Attorney, Agent, or Firm* — Saul Ewing LLP; Kathryn Doyle; Sean P. Ritchie

(57) ABSTRACT

Provided herein are patient-controlled oral liquid-medicine dispenser and deactivation systems. The system includes a dosing container having a defined volumetric capacity and a spillway adapted and configured to allow fluid in excess of the defined volumetric capacity to flow out of the dosing container; a sealed and tamperproof waste receptacle fluidly coupled to the dosing container, the waste receptacle adapted and configured to capture and prevent diversion of liquid medicine dispensed in excess of the defined volumetric capacity of the dosing container; and a suction apparatus extending between a lower region of the dosing container and outside of the dosing container. Also provided herein are methods of administering a medication using the system.

30 Claims, 13 Drawing Sheets

PATIENT-CONTROLLED LIQUID ORAL MEDICINE DISPENSER AND DEACTIVATION SYSTEM

CROSS-REFERENCE TO RELATED APPLICATIONS

The present application claims priority under 35 U.S.C. § 119(e) to U.S. Provisional Patent Application No. 63/366,032, filed Jun. 8, 2022, and U.S. Provisional Patent Application No. 63/418,182, filed Oct. 21, 2022, which applications are incorporated herein by reference in their entirety.

BACKGROUND OF THE INVENTION

Patient-controlled liquid medication administration is commonly achieved invasively including but not limited to intravenous, subcutaneous, epidural, and intrathecal routes via indwelling catheters. These are associated with complexity in setting up, and complications such as infection, bleeding, catheter dislodgment, and scheduled and as-needed catheter replacement. In addition, the invasive mode of medication delivery often must be transitioned to a non-invasive oral format before discharge, an extra step that is stressful and uncomfortable for the patient (due to medication side effects and poor pain control) and jeopardies hospital turnover.

Because non-invasive oral as needed (PRN) medication delivery relies on nursing availability, there are frequently delays in administration due to many demands on nursing staff. This is a well-known phenomenon that negatively impacts patient satisfaction, recovery, and ability to work with physical and occupational therapy. It also causes side effects such as nausea, vomiting, and poor pain control, as well as compensatory behavior from patients who ask for medication with anticipated but not real need. This is particularly detrimental when it comes to opioids for pain management, an issue that will only get worse with the projected nursing shortage over the next 30 years. Moving away from dependence on nursing delivery, efforts have been made to use devices for patient-controlled oral administration of pill medication. However, pills are inherently associated with drug diversion and trafficking when controlled substances such as opioids and benzodiazepines are involved.

SUMMARY OF THE INVENTION

In one aspect, a patient-controlled oral liquid-medicine dispenser and deactivation system includes a dosing container having a defined volumetric capacity and a spillway adapted and configured to allow fluid in excess of the defined volumetric capacity to flow out of the dosing container; a sealed and tamperproof waste receptacle fluidly coupled to the dosing container, the waste receptacle adapted and configured to capture and prevent diversion of liquid medicine dispensed in excess of the defined volumetric capacity of the dosing container; and a suction apparatus extending between a lower region of the dosing container and outside of the dosing container. In some embodiments, the sealed waste receptacle further comprises a neutralizing agent adapted and configured to prevent diversion of liquid medicine by deactivation, solidification, and/or bittering.

In some embodiments, the suction apparatus is detachable. In some embodiments, the suction apparatus and the dosing container are adapted and configured such that the liquid medicine cannot be delivered from the suction apparatus without suction. In some embodiments, the sealed waste receptacle surrounds the dosing container. In some embodiments, the dosing container is separate from the sealed waste receptacle. In some embodiments, the dosing container is separately sealed and tamper proof. In some embodiments, the sealed waste receptacle and dosing container include an optically transparent or translucent window allowing a user to view the contents of the dosing container, but otherwise obscuring the contents of the sealed waste receptacle.

In some embodiments, the system is configured to waste excess medication in the dosing container. In some embodiments, the system includes a pump arranged and disposed to pump the excess medication from the dosing container to the sealed waste receptacle after patient use.

In some embodiments, the system includes a medication measurement device arranged and disposed to measure at least one of an amount of medication consumed by a patient and an amount of medication wasted. In some embodiments, the medication measurement device is selected from the group consisting of a graduated cylinder, a scale, a flow meter, and combinations thereof.

In some embodiments, the system includes at least one electronic communication element arranged and disposed to record data and electronically communicate the recorded data to a remote location. In some embodiments, the electronic communication element is selected from the group consisting of smart chips, near field communication chips, and a combination thereof.

In some embodiments, the system includes an apparatus for filling the dosing container with a preset volume of a solution containing a liquid medication, the apparatus comprising at least one medication reservoir; a pump for delivering the preset volume of the solution to the dosing container, the pump having an inlet and an outlet, and the pump being adapted and configured for fluidic coupling to the at least one medication reservoir; a first delivery conduit having a first end and a second end, the first end being coupled to an outlet of the at least one medication reservoir and the second end being coupled to the inlet of the pump; and a second delivery conduit having a first end and a second end, the first end being connected to the outlet of the pump, the second end being connected to the dosing container. In some embodiments, the pump is at least one of re-programmable, adjustable, password-protected, and lockable. In some embodiments, the pump is a programmable or adjustable patient-controlled pump.

In some embodiments, the system includes at least one security feature configured to prevent dispensing of the solution from the at least one medication reservoir to the dosing container without verification. In some embodiments, the at least one security feature includes a locking device, a security digital keypad, a fingerprint reader, a radio frequency identification (RFID) reader, a facial recognition system, a location tracking device, or combinations thereof. In one embodiment, the at least one security feature includes a security digital keypad and a fingerprint reader.

In some embodiments, the at least one medication reservoir is removable, refillable, and replaceable by an authorized health care provider based on a physician's prescription. In some embodiments, the suction apparatus comprises two components. In some embodiments, the system includes at least one handle. In some embodiments, the liquid medicine is an opioid or a non-opioid.

In another aspect, a method for filling a dosing container with a preset volume of a solution containing a liquid medicine, the method comprising pumping the preset volume of the solution into the dosing container using the patient-controlled oral liquid-medicine dispenser and deactivation system of any one of the embodiments disclosed herein, wherein the dosing container overflows when the pumped volume exceeds the defined volumetric capacity of the dosing container. In some embodiments, medication overflow from the dosing container is deactivated in the sealed and tamperproof waste receptacle. In some embodiments, the deactivated medication is disposable as regular waste. In some embodiments, the medication cannot be consumed from the dosing container while the medication is being pumped to the dosing container.

In a further aspect, a method for administering a preset volume of a solution containing a liquid medicine to a subject in need thereof, the method comprising pumping the preset volume of the solution into the dosing container using the patient-controlled oral liquid-medicine dispenser and deactivation system of any one of the embodiments disclosed herein; and providing the suction apparatus to said patient; wherein the patient ingests the preset volume of the solution containing the liquid medicine from the dosing container through the suction apparatus; and wherein the dosing container overflows when the preset volume exceeds the defined volumetric capacity of the dosing container. In some embodiments, the liquid medicine cannot be delivered from the suction apparatus without suction. In some embodiments, the method further includes providing a sliding scale function. In some embodiments, the sliding scale function permits up to 3 doses to be delivered in one setting. In some embodiments, the method further comprises tracking the amount of medication consumed by the patient over a period of time; and documenting the amount of medication consumed in the patient's medical record.

BRIEF DESCRIPTION OF THE DRAWINGS

For a fuller understanding of the nature and desired objects of the present invention, reference is made to the following detailed description taken in conjunction with the accompanying figures wherein like reference characters denote corresponding parts throughout the several views.

DEFINITIONS

Figure 1:
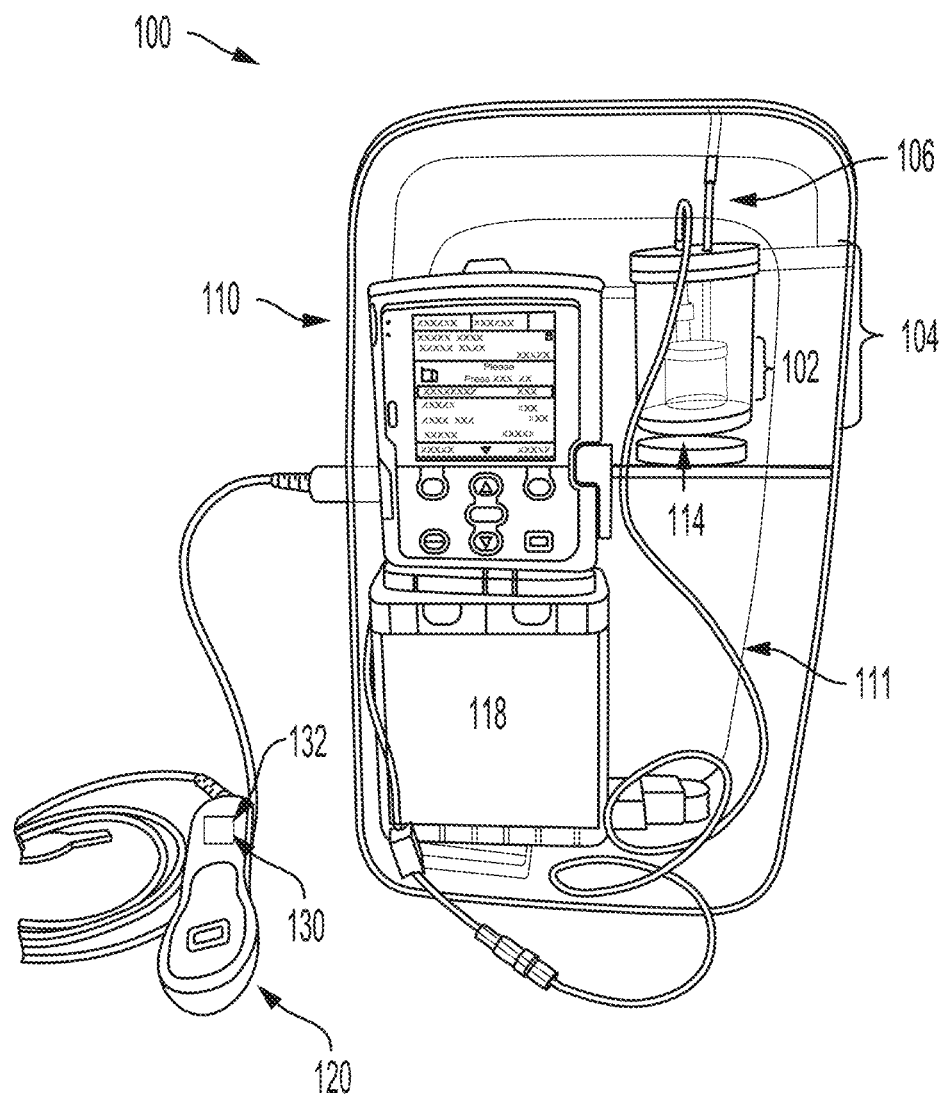
FIG. 1 is an image of an oral patient-controlled liquid medicine dispenser and deactivation system according to an embodiment of the invention.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Patient controlled liquid oral medication dispenser and deactivator (PCDD) is a novel and safe device to facilitate the self-administration for controlled and non-controlled substances. The PCDD disclosed herein may be used for dispensing medication to both adults and pediatric patients, empowering them to take control of their medical management including pain management. The PCDD also provides the additional benefits of decreased healthcare-worker demand, decreased opioid misuse and diversion, and improved healthcare economics.

At the individual patient level, this invention has the documented benefits of patient-controlled delivery of medication (in a non-invasive oral format) and controlled medication deactivation, thus eliminating the need to return controlled substances such as opioids to authorities or pharmacies at the end of treatment. At the community level, this invention helps with controlled substance management by minimizing drug diversion and drug trafficking during treatment and minimizing unused medication such as opioids and other controlled substances in the community by including a patient-controlled medication deactivation mechanism when treatment is complete. This essentially abolishes the need to return unused controlled substances such as opioid pills to dedicated return locations, which will help with decreasing loose pills available in the community and/or decrease the risks of mobility and mortality related to opioid misuse (use of opioids not prescribed to the correct person for the correct indication).

Referring now to FIG. 1, one embodiment of the invention provides a hand-held patient-controlled liquid-medicine dispenser 100. The hand-held unit 100 includes a medication reservoir 118, a dosing container 102 fluidly coupled to the medication reservoir 118, and a patient-controlled pump 110 arranged and disposed to pump a precise dose of any suitable controlled and/or non-controlled medication from the medication reservoir 118 to the dosing container 102. The dosing container 102 may be fluidly coupled to the medication reservoir 118 through any suitable mechanism, such as, but not limited to, tubing 111. In some embodiments, the dosing container 102 is sized exactly per the liquid medication dose such as, for example, through interchangeable and/or adjustable dosing containers. Alternatively, in some embodiments, the dosing container 102 is sized to hold more than one dose, including, but not limited to, at least 2 doses, at least 3 doses, or up to 3 doses of the medication.

The patient-controlled pump 110 may be activated through any suitable mechanism, such as, but not limited to, through a patient controlled remote 120. In some embodiments, the hand-held unit 100 includes one or more security features 130, such as a delivery security features 132 configured to prevent unauthorized delivery of the medication from the medication reservoir 118 to the dosing container 102. Suitable delivery security features 132 include, but are not limited to, a code key pad, a finger print reader, facial recognition, other biometric security features, or any other patient-specific security feature. For example, in some embodiments, the hand-held device 100 includes a code key pad, a finger print reader, and/or facial recognition, such that the medication cannot be pumped to the dosing container 102 until dual confirmation has been provided by the patient.

When the patient requests medication (and the patient-controlled pump 110 is eligible to deliver medication), at least one dose of liquid medication is pumped from the medication reservoir 118 by the patient-controlled pump 110 through the tubing 111 into the dosing container 102. The tubing 111 may be attached to any suitable portion of the dosing container 102, such as, but not limited to, the bottom, a side, a lid 107, or a combination thereof. The patient-controlled pump 110 includes any suitable pump and may pump the medication from the medication reservoir 118 to the dosing container 102 in any suitable manner. Suitable pumps include, but are not limited to, a PCA pump, an elastomeric pump, an IV pump, or any other pump capable of dispensing a set amount of medication. For example, in one embodiment, the dosing container 102 may be fluidly coupled to the medication reservoir 118 through the patient-controlled pump 110, such that the patient-controlled pump 110 can draw the medication directly from the medication reservoir 118 and then deliver the medication to the dosing container 102. In another embodiment, the patient-controlled pump 110 may pump the medication from the medication reservoir 118 to the dosing container 102 without contacting the medication (e.g., rollers contacting tubing 111 extending between the medication reservoir 118 and the dosing container 102, generating positive or negative pressure, or through any other suitable method).

After the liquid medication has been delivered to the dosing container 102, the patient can then consume the liquid medication. In some embodiments, the hand-held unit 100 includes a suction apparatus 106 arranged and disposed to permit the patient to drink the liquid medication. The suction apparatus 106 includes any suitable apparatus for delivering the medication from the dosing container 102 when suction is applied thereto, such as, but not limited to, a straw. In some embodiments, the suction apparatus includes one or more anti-spill features. For example, the suction apparatus may form a liquid tight seal with the dosing container and include a check valve, such that a suction action is required to draw the medication from the dosing container (i.e., directly to the patient's mouth). The liquid tight seal also reduces or eliminates the introduction of air when suction is applied to the suction apparatus 106. Additionally or alternatively, in some embodiments, the suction apparatus 106 or system includes a mechanism to prevent suction of extra air and/or to ensure a full dose is being suctioned out. One such mechanism includes priming the system with a specific liquid medication before use (e.g., up to the outlet of the suction apparatus 406). In such embodiments, the primed liquid medication acts like a water seal, preventing the patient from suctioning air following the consumption of a dose and/or ensuring the entire dose has been suctioned out.

Figure 2:
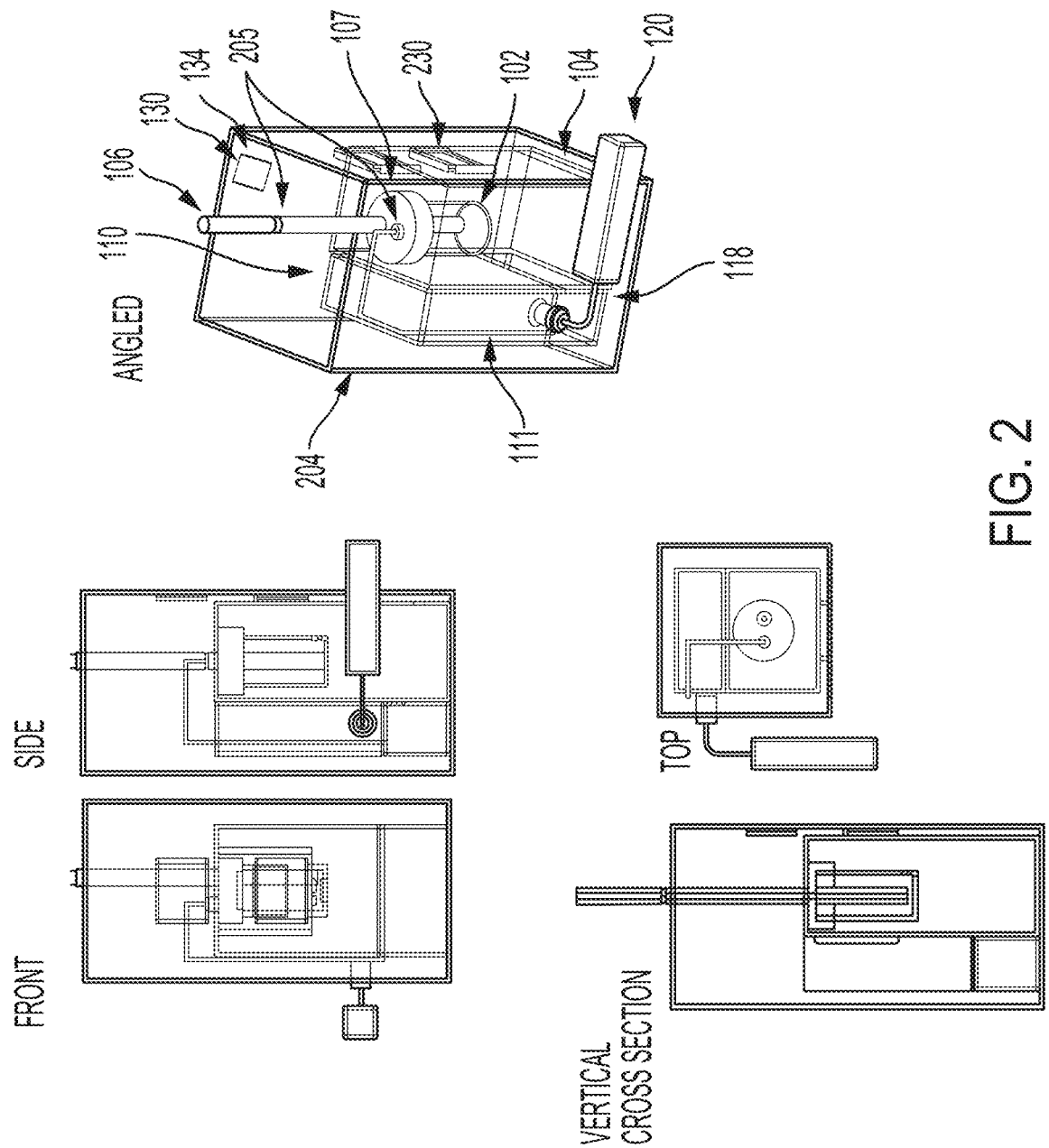
FIG. 2 is a schematic of an oral patient-controlled liquid medicine dispenser and deactivation system according to an embodiment of the invention.

In some embodiments, the suction apparatus 106 includes one or more features to reduce or eliminate unauthorized consumption of medication after delivery to the dosing container 102. For example, the suction apparatus 106 may be specially designed such that it can be removed by the patient to prevent others (e.g., family members and children) from drawing medication out of the dosing container 102. In some embodiments, the removable suction apparatus 106 is mechanically locked to the device in a secure manner. One suitable removable suction apparatus 106 includes a removable straw or portion of a straw that may be attached/removed. In such embodiments, the straw or portion thereof may be removably attached through any suitable interface 205, such as, but not limited to, a luer lock (FIG. 2). The removable suction apparatus 106 may also be disposable/replaceable (e.g., a removable, disposable upper portion of a straw).

Additionally or alternatively, the security feature 130 may include a consumption security feature 134 (FIG. 2) to restrict or prevent access to the medicine through the suction apparatus 106. Suitable consumption security features 134 may be combined with any suitable arrangement for consuming the medicine (e.g., a fixed suction apparatus, a removable suction apparatus, any other configuration permitting consumption) and include, but are not limited to, a code key pad, a finger print reader, facial recognition, other biometric security features, valves, other articles for selectively restricting fluid flow, any other patient-specific security feature, or combinations thereof. In some embodiments, for example, the suction apparatus 106 may include a valve or other article that is linked to a code key pad, finger print reader, and/or facial recognition, such that the valve or other article will not permit fluids to be sucked through the suction apparatus 106 until a patient's identity has been confirmed through the key pad, finger print reader, and/or facial recognition. In some embodiments, the consumption security feature 134 prevents consumption of the medicine while it is being delivered to the dosing container 102. For example, the valve or other article may be arranged and disposed to prevent consumption of the medicine while it is being delivered to the dosing container 102, independent of or in combination with any other security feature 130 (e.g., corresponding valves for delivery and consumption, where only one valve can be open at a time). The delivery security feature 132 and the consumption security feature 134 may be the same or separate and, as will be appreciated by those skilled in the art, may each be positioned anywhere on the system 100 (e.g., on the remote 120, an outer surface of the system 100, or any other suitable location).

The hand-held unit 100 may also include one or more features to reduce or eliminate diversion of any medication that is not consumed. For example, in some embodiments, the hand-held unit 100 includes a separate waste receptacle 104 fluidly coupled to the dosing container 102 and/or the medication reservoir 118. In such embodiments, any excess medication remaining in the dosing container 102 and/or the medication reservoir 118 is drained into the waste receptacle 104, where it can be deactivated before being discarded. Any suitable criterion may be used to determine that the medication is excess, such as, but not limited to, time since delivery to the dosing container 102, time since last consumption, request for another dose, entering of a code into a keypad, patient control, authorized health care worker (e.g., nurse, doctor) control, or any other suitable indication that a remaining portion of a medication should be considered waste. For example, if the patient does not drink the entire dose prior to expiration of a scheduled interval, the remaining excess medication will be removed from the dosing container 102 via a drain hole into the waste receptacle 104. In another example, the patient may input a code into a keypad (e.g., delivery security feature 132), the inputting of the code causing the entire contents of the medication reservoir 118 to be emptied into the waste receptacle 104, either directly or through the dosing container 102.

Once in the waste receptacle 104, the excess medication can be instantly chemically deactivated (e.g., via a neutralizing or deactivating agent 114, such as activated charcoal, solidifier, bittering agent, Deterra® Drug Deactivation and Disposal Pouches, or DisposeRx powder packets which utilize solidifying cross-linking chemical polymers to sequester medications). This excess deactivated medication is non-consumable, neutralized, and/or no longer pharmacologically active, and can then be discarded without concern for diversion. In some embodiments, the deactivated medication is disposable as regular trash/waste, without the need for special treatment/handling. In some embodiments, the waste receptacle 104 may be removably attached to any other element of the dispenser/system 100. For example, in some embodiments, as illustrated in FIG. 2, the waste receptacle 104 is attached to the dosing container 102, the pump 110, the medication reservoir 118, or any other suitable container (e.g., an outer container 204) through any suitable attachment member 230. Suitable attachment members 230 include, but are not limited to, clips, snaps, ties, locks, or any other suitable member for securing the waste receptacle 104 to another element.

In some embodiments, the one or more features to reduce or eliminate diversion are directed to reducing or eliminating tampering. For example, the emptying of the dosing container 102 and/or the medication reservoir 118 may be triggered by tampering with the system 100, such as, for example, in connection with attempted unauthorized access. This could include entering an incorrect code a certain number of times, attempting to open a sealed portions of the system 100, an impact detection, or any other indication of an attempt to improperly access the medication. Additionally or alternatively, the tubing 111 may lock into the system 100 and/or be retractable. For example, the tubing 111 may be locked into the medication reservoir 118, such that it cannot be unhooked, and/or configured to retract into the medication reservoir 118 and/or another portion of the system 100 if tampering is detected (.e.g., tension is removed by cutting the tubing or disconnecting a second end thereof).

Referring now to FIGS. 3-12, an embodiment of the invention provides an oral patient-controlled liquid-medicine dispenser and deactivation system 400. Although the hand-held unit 100 and the system 400 are described separately, as will be appreciated by those skilled in the art, the individual features discussed in connection with the unit 100 may be included in the system 400, and vice versa. In this regard, corresponding reference characters have been employed (e.g., pump—110 and 410) to help illustrate like elements. As such, unless stated otherwise, each element and feature discussed in connection with either the hand-held unit 100 or the system 400 is expressly disclosed as being included with the other.

Figure 3:
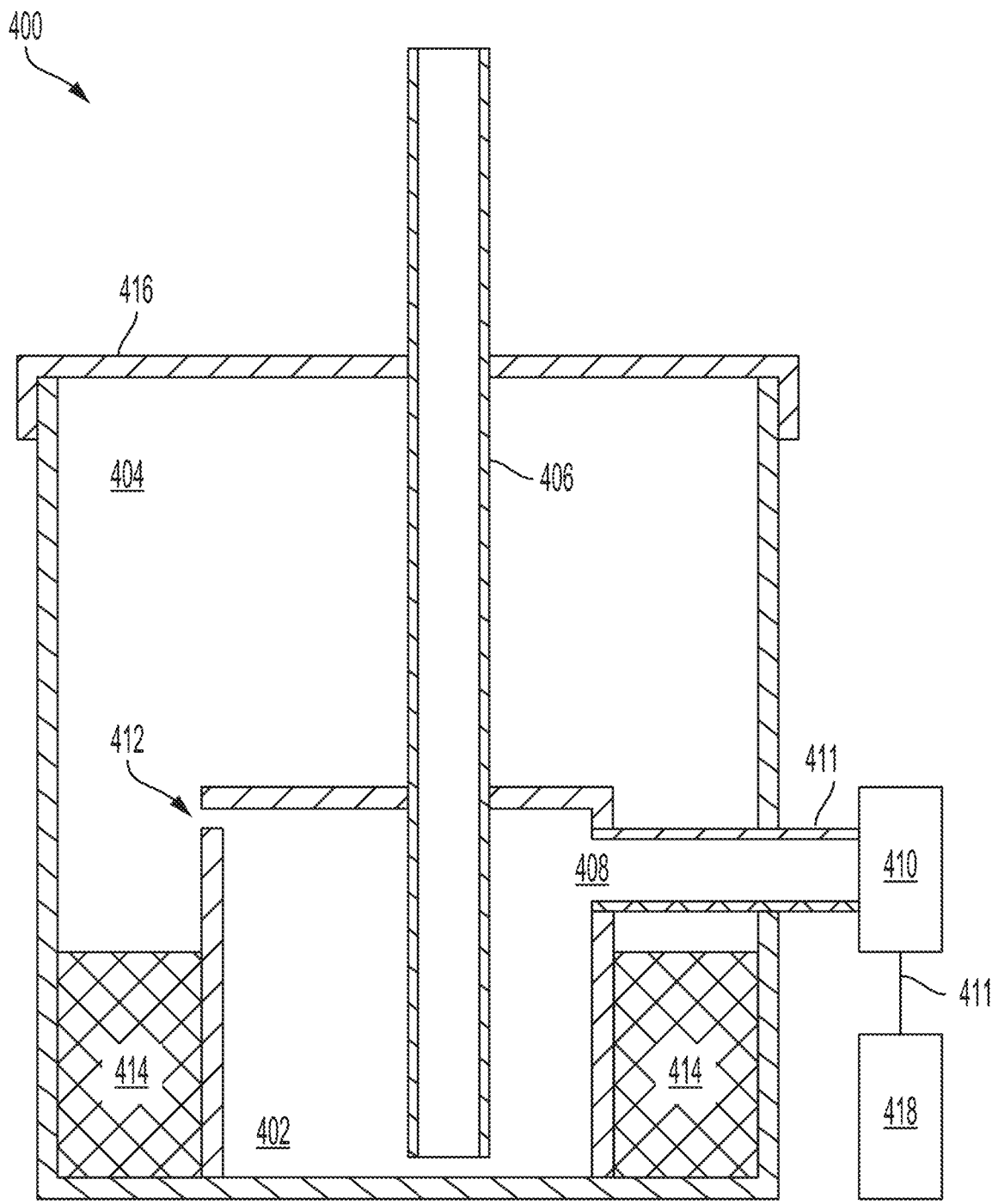
FIG. 3 is a cross-sectional side view of an oral patient-controlled liquid medicine dispenser and deactivation system according to an embodiment of the invention.
Figure 6:
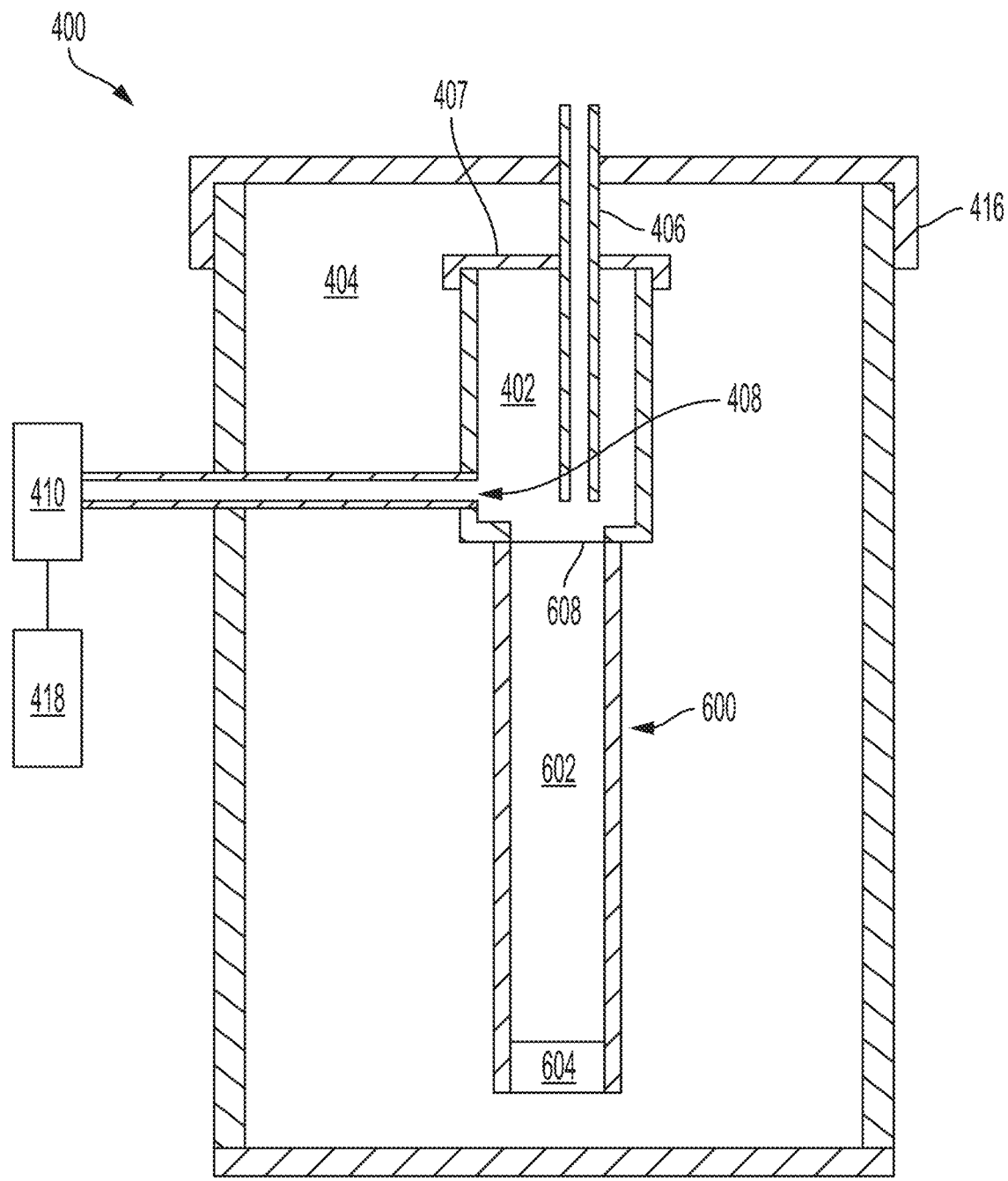
FIG. 6 is a cross-sectional side view of an oral patient-controlled liquid medicine dispenser and deactivation system according to an embodiment of the invention.
Figure 7:
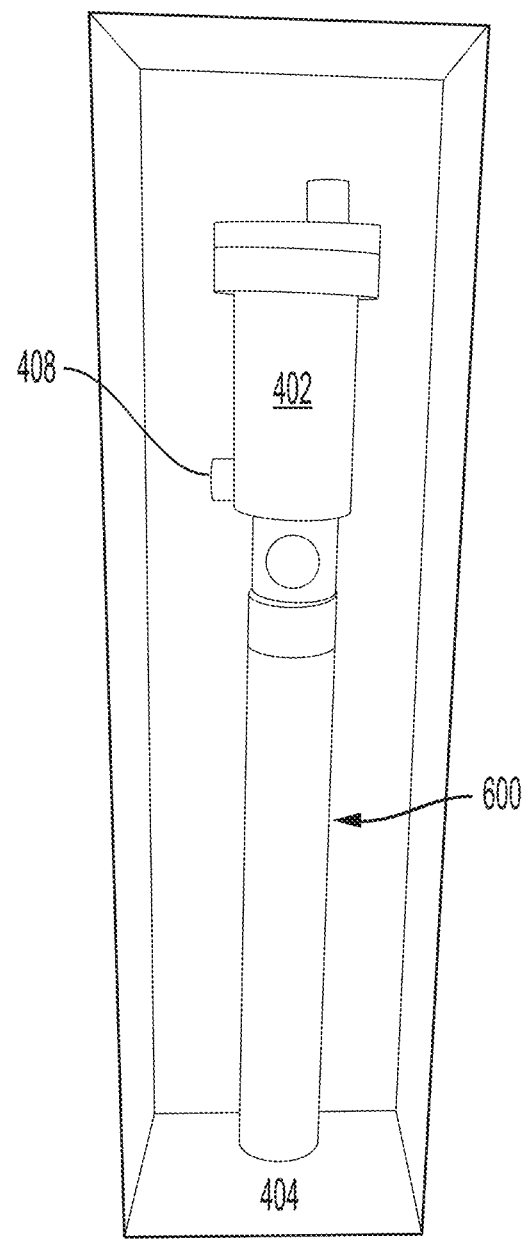
FIG. 7 is an image of an inner receptacle and measuring device within an outer receptacle according to an embodiment of the invention.
Figure 8:
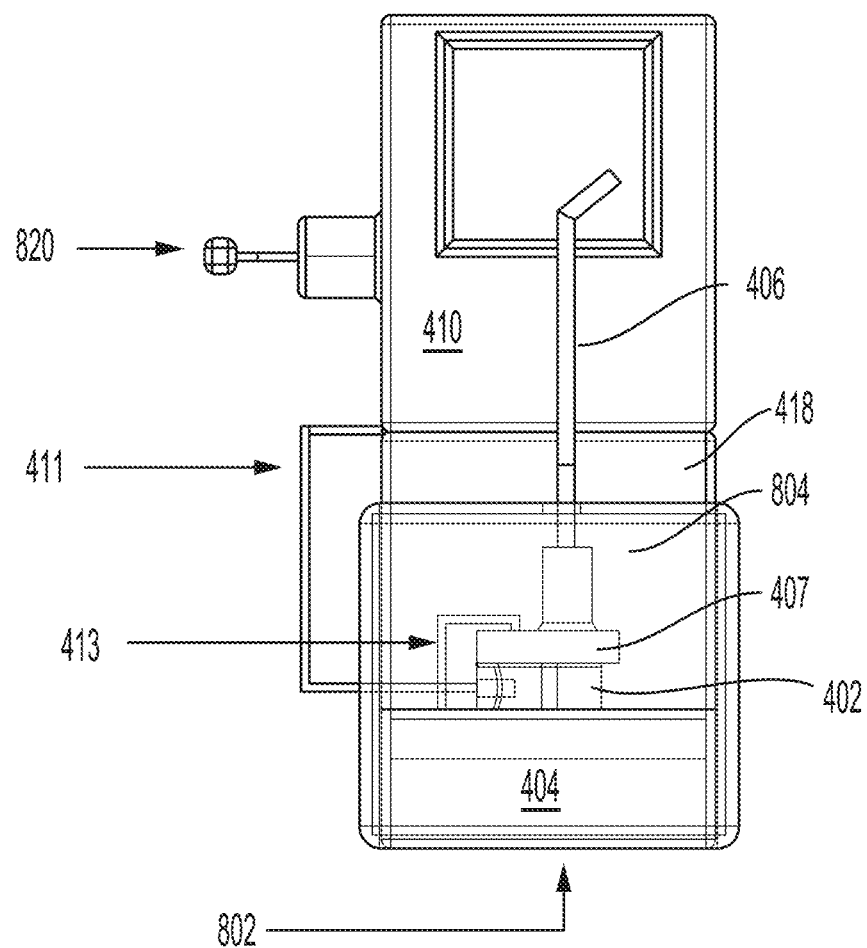
FIG. 8 is a schematic of an oral patient-controlled liquid medicine dispenser according to an embodiment of the invention.

The system 400 includes a dosing container 402, a sealed waste receptacle 404, and a suction apparatus 406 extending between a lower region of the dosing container 402 and an outside of the system 400. The system 400 may also include one or more optional handles 401 coupled to any portion thereof (FIGS. 4 and 9) and/or a patient-controlled remote 820 (FIG. 8). Although the dosing container 402 in FIG. 3 is depicted within and on a lower surface of the sealed waste receptacle 404, the dosing container 402 can be in other locations, e.g., raised above a lower surface of the sealed waste receptacle 404 and/or outside the waste receptacle 404. For example, in some embodiments, as illustrated in FIGS. 6-7, a measurement device 600 is positioned between the dosing container 402 and the lower surface of the sealed waste receptacle 404. Alternatively, as illustrated in FIGS. 8-12, the dosing container 402 is positioned outside the waste receptacle 404, within a separate outer receptacle 804. The outer receptacle 804 may contain the dosing container 402 and/or the waster receptacle 404 to reduce or eliminate access thereto. In some embodiments, positioning the dosing container 402 above a lower surface and/or outside of the sealed waste receptacle 404 provides greater overflow capacity.

In some embodiments, regardless of the positioning of the dosing container 402, the amount of medicine remaining therein is visible to the patient. For example, in some embodiments, the sealed waste receptacle 404 and/or the separate outer receptacle 804 include a transparent surface or portion of a surface through which the dosing container 402 may be viewed. Additionally or alternatively, in some embodiments, the device/system includes an article for determining the amount of medicine in the dosing container 402. One such article includes, but is not limited to, a ruler (e.g., a graduated mL ruler) secured or formed (e.g., engraved) on a surface of the device/system.

The dosing container 402 can have a defined volumetric capacity (e.g., measured in a unit such as mL). For example, the dosing container 402 may include a volume of between 2 ml and 10 ml, about 2 ml, about 2.5 ml, about 4 ml, about 5 ml, about 8 ml, about 10 ml, or any suitable combination, sub-combination, range, or sub-range thereof. The dosing container 402 includes any suitable size and/or shape defining the volumetric capacity, such as, but not limited to, a cup or container having any shape capable of holding liquid therein, a syringe, or any other suitable configuration. In some embodiments, the dosing container 402 includes a dosing container lid 407. The dosing container lid 407 may include any suitable shape, such as, but not limited to, flat (FIG. 4), rounded (FIG. 5), any other suitable shape for containing a fluid within the dosing container 402, or a combination thereof. Additionally, the dosing container lid 407 may include one or more openings for receiving, dispensing, and/or discarding fluids (e.g., medicines). In some embodiments, the dosing container 402 is adjustable (e.g., via threaded adjustment using a key or an insert) or swappable (e.g., before issuance to a patient) by a medical professional to accommodate various doses within a sealed portion of the system 400 (e.g., through a threaded connection, snap fittings, tabs, and the like). In such embodiments, the dosing container 402 may be adjusted or swapped to provide a desired capacity, such as, but not limited to, the equivalent of a single dose or multiple doses of the medication.

The dosing container 402 can include an opening 408 for receiving medicine from a pump 410. In some embodiments, the pump 410 is patient-controlled, but programmed with restrictions that limit administration of the medicine. For example, the pump 410 may be programmed to limit how often medicine can be administered (e.g., how many doses may be distributed over a specific period of time), to limit the size of each dose, to limit how many doses may be dispensed at one time (e.g., to provide a sliding scale, where one or more doses may be dispensed at once), or to define any other limitation on the administration of the medicine. Additionally or alternatively, in some embodiments, the pump 410 includes one or more libraries loaded thereon. For example, the pump 410 may include multiple libraries preloaded by a pharmacy/authorized health care provider (e.g., a pharmacist, nurse, or physician). In some embodiments, the loading and/or preloading of the libraries on the pump 410 reduce or eliminate unique coding of the pump 410 for each patient.

Pump 410 may be coupled to any suitable medication source. For example, in some embodiments, pump 410 contains or is in fluidic communication with a medication reservoir 418 that can be removable and refillable or replaceable by an authorized health care worker and/or in a pharmacy or authorized healthcare provider. The pump 410 may be fluidly coupled to the medication reservoir 418 and/or the dosing container 402 in any suitable manner, such as, but not limited to, through tubing 411. In other embodiments, a patient-controlled pump 410 can be engineered specifically for an in-home environment, e.g., by using lower-cost disposable materials. In some embodiments, the pump 410 can be an intravenous patient-controlled pump.

Figure 4:
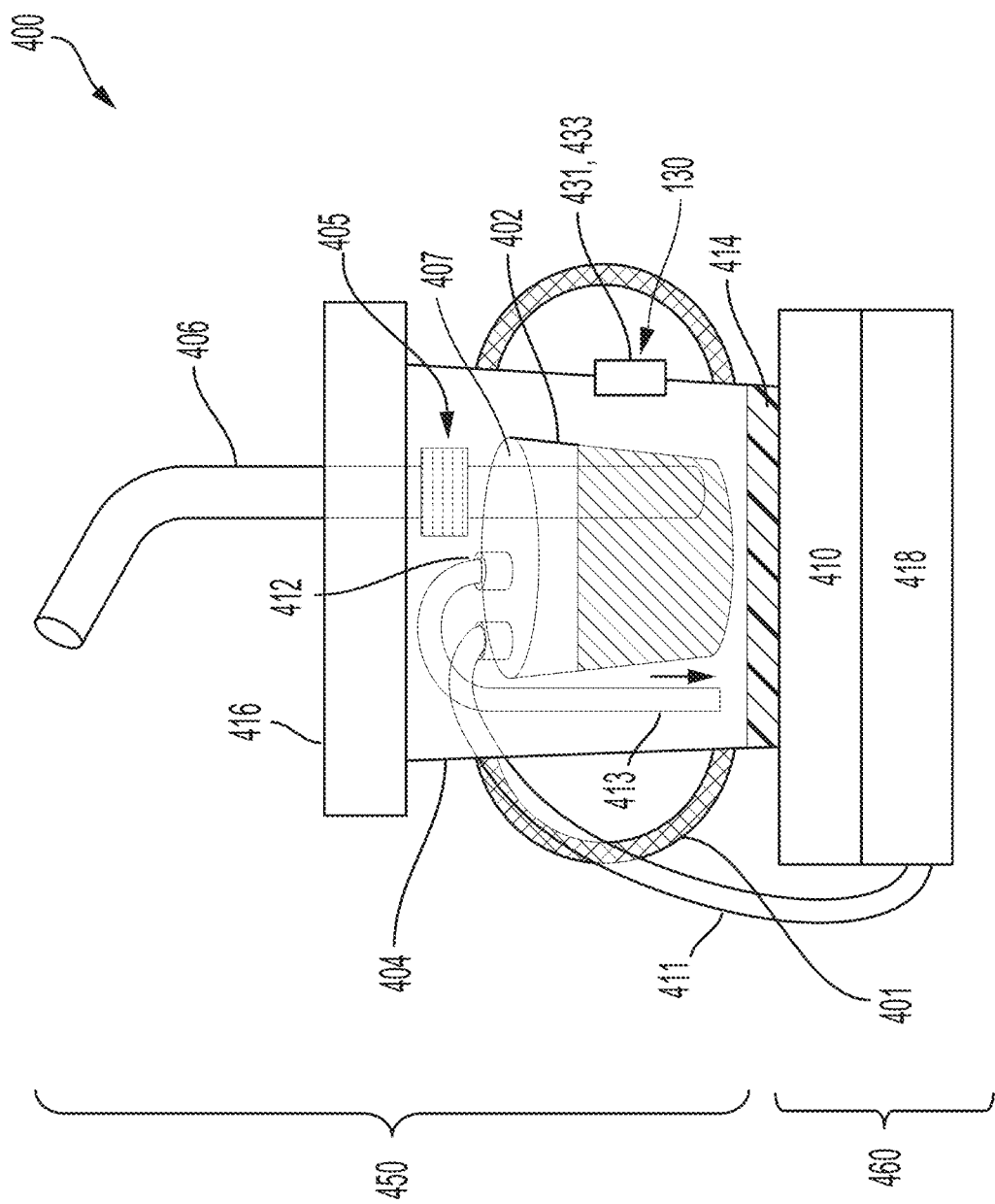
FIG. 4 is an image of an oral patient-controlled liquid medicine dispenser and deactivation system according to embodiments of the invention.

The dosing container 402 can include an outlet 412 adapted and configured to convey fluid in excess of the defined volumetric capacity out of the dosing container 402. In some embodiments, as illustrated in FIG. 3, the outlet 412 includes a spillway arranged and disposed to permit excess fluid to flow out of the dosing container 402. Additionally or alternatively, in some embodiments, as illustrated in FIG. 4, the outlet 412 includes a drain. In some embodiments, the drain includes drain outlet tubing 413 and/or a drain pump arranged and disposed to actively transport medicine from within the dosing container 402 to the waste receptacle 404. The drain pump includes any suitable pump for transporting liquid from the dosing container 402, and may be programmable or adjustable, lockable (e.g., electronically or elastomerically), or a combination thereof.

Medicine that flows out of the dosing container 402 is contained within the sealed waste receptacle 404 and cannot be practically accessed by anyone, including the patient, family members, health care workers, or any other individual. For example, the size and position of the outlet 412 can make it difficult, if not impossible to tilt the system 400 in order for any appreciable amount of medicine to flow back from the sealed waste receptacle 404 into the dosing container 402. The medication may also be instantaneously deactivated and solidified upon reaching the waste receptacle 404, thus preventing flow of the wasted medication back into the dosing container 402 or otherwise out of the system. Additionally or alternatively, the drain pump may prevent the flow of liquid from the sealed waste receptacle 404 into the dosing container. In some embodiments, the outlet 412 can include a check valve (e.g., one way valve in the spillway of FIG. 3, one-way luer lock within the drain outlet tubing 413 of FIG. 4) that only permits fluid flow from the dosing container 402 to the sealed waste receptacle 404. The outlet 412 can be on the side or top of the dosing container 402.

In order to frustrate diversion by breaching the sealed waste receptacle 404, the sealed waste receptacle 404 can further include a neutralizing agent 414 designed to deactivate the medicine and/or change its form such that diversion is impractical or unpalatable. For example, the neutralizing agent 414 can be activated charcoal, a solidifying powder (e.g., available from Medline Industries, LP of Northfield, Illinois), a bittering agent that modifies the taste of the medicine, Deterra® Drug Deactivation and Disposal Pouches, and/or DisposeRx powder packets which utilize solidifying cross-linking chemical polymers to sequester medications. A check valve associated with the outlet 412 can prevent the neutralizing agent 414 from entering the dosing container 402. The waste receptacle 404 may include any suitable amount of neutralizing agent 414. In some embodiments, the amount of neutralizing agent 414 is calculated based on the amount of medication in the medication reservoir 418. For example, the waste receptacle 404 may include sufficient neutralizing agent 414 to deactivate all of the medication in the medication reservoir 418, ensuring that none of the medication can be diverted even if it is not consumed by the patient.

In some embodiments, the sealed waste receptacle 404 includes a lid 416. In such embodiments, when the dosing container 402 is positioned within the waste receptacle 404, the lid 416 permits installation and/or adjustment of the dosing container 402 to accommodate a specified dosage volume. Additionally or alternatively, in some embodiments, the lid 416 permits installation of the neutralizing agent 414 in the field or during manufacturing. In some embodiments, the lid 416 may be permanently attached using a variety of techniques and materials, including one-way mechanical devices, adhesives, ultrasonic welding, an interference fit, fasteners, and the like. For example, in some embodiments, after installation and/or adjustment of the dosing container 402, and/or installation of the neutralizing agent 414, the lid 416 is permanently attached through a one-way mechanical device.

At least a portion of suction apparatus 406 can be removably coupled to the dosing container 402, e.g., to prevent use of system 400 by unauthorized users such as personnel in a health care facility and family members, particularly children. A variety of interfaces 405 can be utilized including a Luer connector (FIGS. 2 and 4), a screw on connection for a portion of the suction apparatus 406, a screw on connection for a portion of the suction apparatus 406 with a one-way luer lock (FIG. 4), a lock for a full suction apparatus 406 (FIG. 5), or any other suitable locking mechanism. Additionally or alternatively, a check valve can be provided to require mouth suction or hand pump suction action in order to deliver medication directly to the patient's mouth. The same valve or a different valve may also prevent backflow from the suction apparatus 406 into the dispensing container 402 and/or prevent access to the medication via suction while fluid is being dispensed to the dosing container 402 (e.g., during delivery of a dose or wasting of medication from the medication reservoir through the dosing container).

Figure 5:
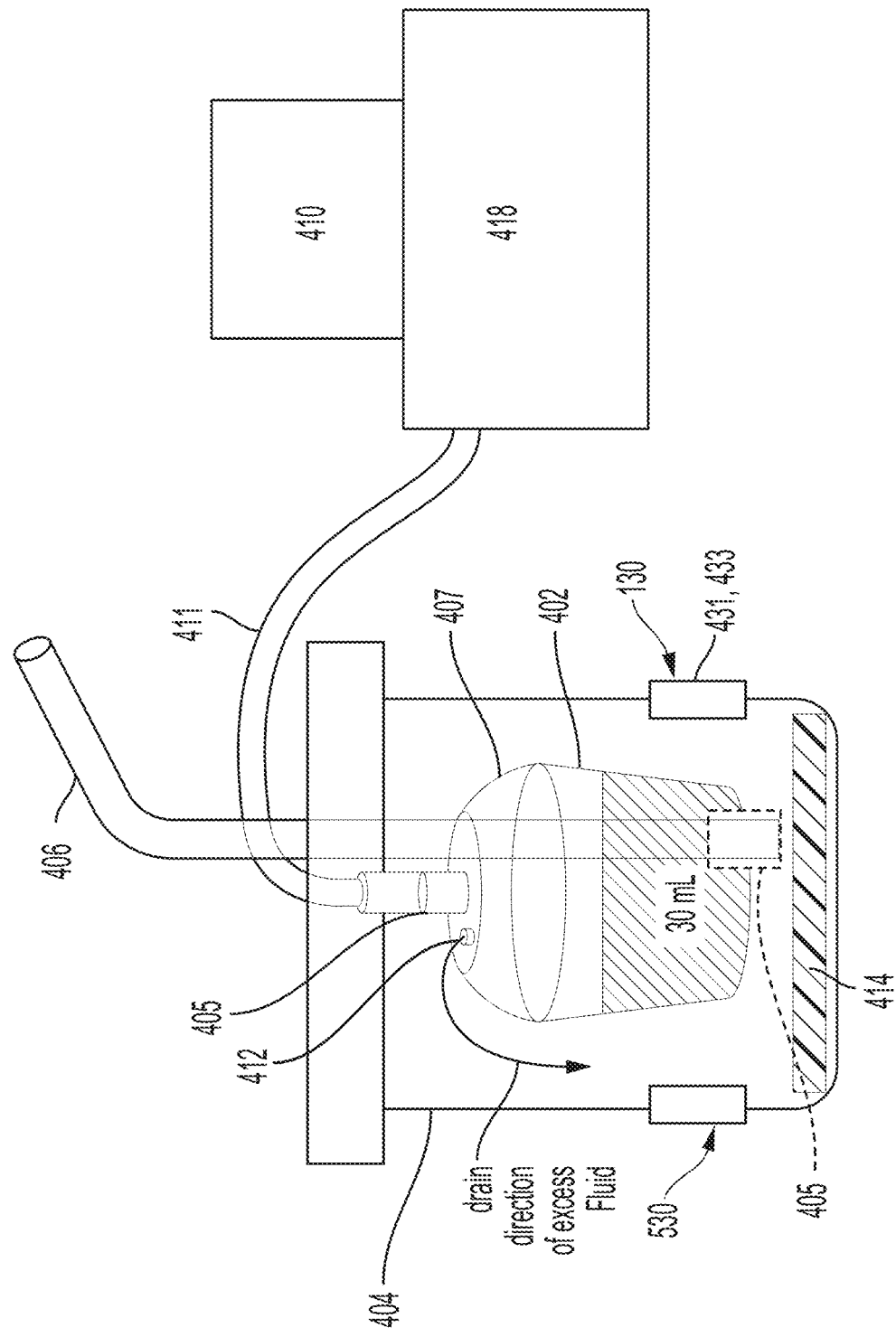
FIG. 5 is an image of an oral patient-controlled liquid medicine dispenser and deactivation system according to embodiments of the invention.

In some embodiments, at least a portion of the patient-controlled liquid-medicine dispenser according to any of the embodiments disclosed herein is disposable. For example, in some embodiments, as illustrated in FIGS. 4 and 5, the dosing container 402, the waste receptacle 404, and/or the suction apparatus 406 form a disposable portion 450, while the medication reservoir 418 and/or pump 410 form a re-usable portion 460. In such embodiments, the medication reservoir 418 is re-fillable, permitting the medication reservoir 418 and pump 410 to be used and/or re-used with different patients, medications, and/or disposable portion 450 configurations. At least a portion of the suction apparatus 406 may be separately disposable, such that a new suction apparatus (FIG. 5) or a new portion of a suction apparatus (FIG. 4) may be used with each dose.

In some embodiments, the patient-controlled liquid oral medicine dispenser disclosed herein includes a measurement device 600 arranged and disposed to measure an amount of medication that is not consumed by the patient (i.e., wasted). The measurement device 600 may include any suitable device for measuring liquid amounts. For example, in some embodiments, as illustrated in FIGS. 6-7, the measurement device 600 includes a graduated cylinder 602 with exact volume marks. The dosing container 402 and the graduated cylinder 602 may be positioned in any suitable arrangement for transferring the fluid from the dosing container 402 to the graduated cylinder 602. For example, in one embodiment, a top portion of the graduated cylinder 602 is aligned with a sealable opening 608 in a bottom portion of the dosing container 402. The sealable opening 608 includes any configuration for selectively permitting fluid to drain from the dosing container 402 to the graduated cylinder 602, but not from the graduated cylinder 602 back into the dosing container 402, such as, but not limited to, an electronic timing valve. Alternatively, the graduated cylinder 602 may be positioned anywhere near the dosing container 402, and the fluid within the dosing container 402 may be pumped to the graduated cylinder 602.

In some embodiments, the graduated cylinder 602 includes a release feature 604 at a bottom portion thereof. The release feature includes any suitable feature for selectively maintaining a fluid within the graduated cylinder 602, such as, but not limited to, a stopcock. When in use, any fluid remaining in the dosing container 402 may be drained into the graduated cylinder 602, where it is held until the release feature 604 is actuated (e.g., until the fluid can be measured). Once the release feature 604 is actuated, the fluid can drain from the graduated cylinder 602 into a waste container, such as the sealed waste receptacle 404. In embodiments where the graduated cylinder 602 and the release feature 604 are contained within the sealed waste receptacle 404, the system includes one or more features facilitating access and/or actuation of the release feature 604 from outside the sealed waste receptacle 404. Suitable features for accessing and/or actuating the release feature 604 include, but are not limited to, a moveable member extending from the release feature 604 within the sealed waste receptacle 404 to an outside surface of the sealed waste receptacle 404, an access panel and associated opening extending from an outer surface of the sealed waste receptacle 404 to the release feature 604, or any other suitable mechanism for actuating the release feature 604 without providing access to liquids within the sealed waste receptacle 404.

Figure 9:
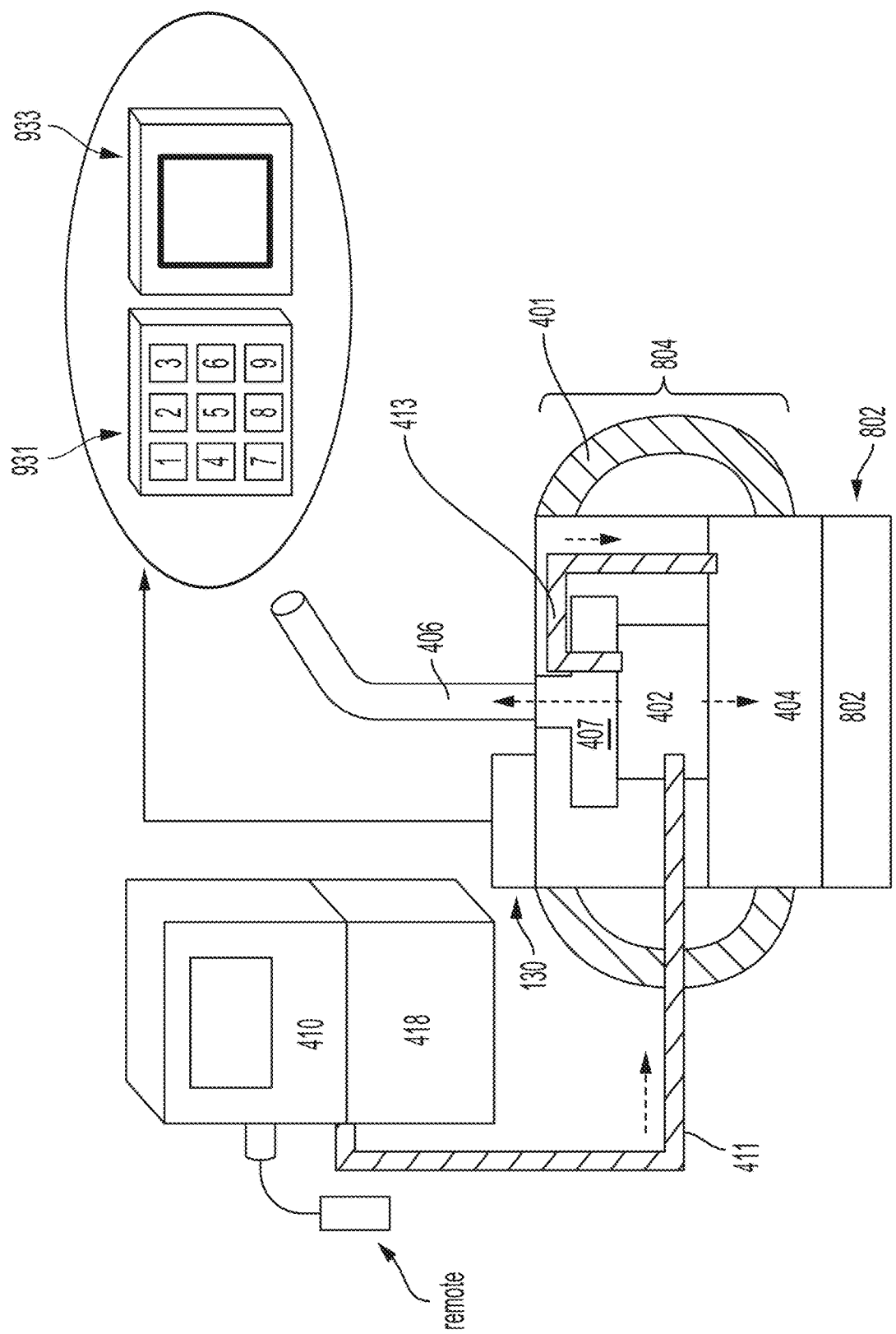
FIG. 9 is a schematic of an oral patient-controlled liquid medicine dispenser including a security device, according to an embodiment of the invention.
Figure 10:
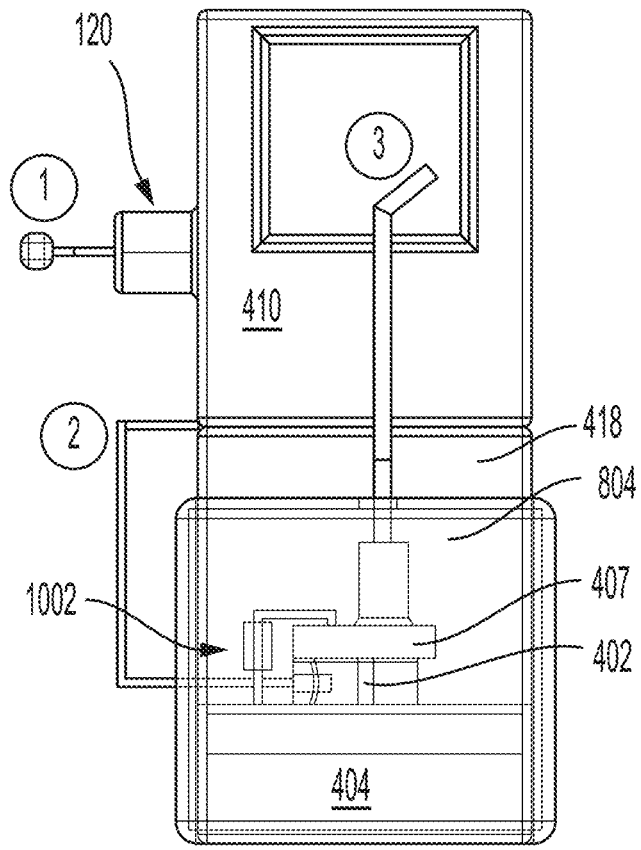
FIG. 10 is a schematic of an oral patient-controlled liquid medicine dispenser according to an embodiment of the invention.

Additionally or alternatively, in some embodiments, as illustrated in FIGS. 8-9, the measurement device 600 includes a scale 802. The scale is positioned to support a waste reservoir or other waste container, such that the scale 802 can measure the weight of the waste reservoir or other waste container. In such embodiments, the scale 802 measures changes in weight of the waste reservoir, which is translated to an amount of fluid (i.e., medication dispensed and wasted) in the system. Turning to FIG. 10, in some embodiments, the measurement device 600 includes a flow meter 1002. The flow meter 1002 may be positioned on any portion of the system where a flow of fluid can be measured to determine an amount of fluid not consumed by the patient. For example, the flow meter 1002 may be positioned on drain tubing that conveys the fluid from the dosing container 402 to the waste receptacle 404, on medication tubing that conveys fluid to the dosing container 402, on the suction apparatus 406, or a combination thereof. Although illustrated separately, as will be appreciated by those skilled in the art, the disclosure is not so limited and any combination of measurement devices 600 may be used.

The measurement device 600 may also be arranged and disposed to measure the amount of medication consumed by the patient. In some embodiments, the measurement device 600 directly measures the amount of medication consumed. For example, the flow meter 1002 may be positioned on any portion of the system where a flow of fluid can be measured to determine an amount of fluid consumed by the patient. One such portion of the system includes, but is not limited to, the suction apparatus 406. In another example, the scale 802 may be arranged and disposed to measure the weight of the dosing container 402 and/or the waste receptacle 404 upon delivery of the medication and again upon wasting, or continuously from delivery to wasting, where any change in weight is converted to an amount consumed. Additionally or alternatively, in some embodiments, the measurement device 600 indirectly measures the amount of medication consumed. For example, the measurement device 600 may be arranged and disposed to measure the amount of medication that has been wasted, and subtract that from the amount of medication that has been delivered to the dosing container 402.

In some embodiments, when measuring an amount of medication that is wasted, consumed, or both, the system 400 is also configured to determine whether there is any medication remaining in the dosing container 402. For example, in some embodiments, before measuring an amount wasted and/or consumed, the system 400 measures the weight of the dosing container 402 and compares it to an empty weight thereof, determines whether the dosing container 402 has been wasted since the last delivery of medication, measures the total flow of liquid into and out of the dosing container 402, utilizes any other suitable method for detecting medication in the dosing container 402, or a combination thereof.

Using the measurement devices and methods disclosed herein, the system can automatically, mechanically, and/or electronically track the amount of medication being consumed/wasted. This information can be used to remotely adjust the patient's dosing; automatically and/or electronically document the patient's consumption, outcome (e.g., pain scores), and/or breathing rate (e.g., side effects of opioid overdose); automatically and/or electronically detect tampering; or a combination thereof.

Exemplary Materials

As will be appreciated by one or ordinary skill in the art, the invention provided herein can be fabricated from a variety of materials such as plastic, rubber, metal, and the like by use of various manufacturing techniques such as molding, casting, machining, and the like. For example, components can be formed from polymeric materials such as polypropylene (PP), polyethylene terephthalate (PET), polycarbonate (PC), copolyesters (e.g., PTCG and copolyesters available under the TRITAN™ mark from Eastman Chemical Company of Kingsport, Tenn.), polyphthalate carbonate (PPC), and the like.

Various components can be optically transparent, translucent, and/or opaque. In one embodiment, at least the sealed waste receptacle 404 can be optically opaque except for a viewing window that permits viewing of at least a portion of the dosing container 402. Otherwise, the internal structure and/or contents of the sealed waste receptacle 404 can be shielded from view.

Security Features

Figure 11:
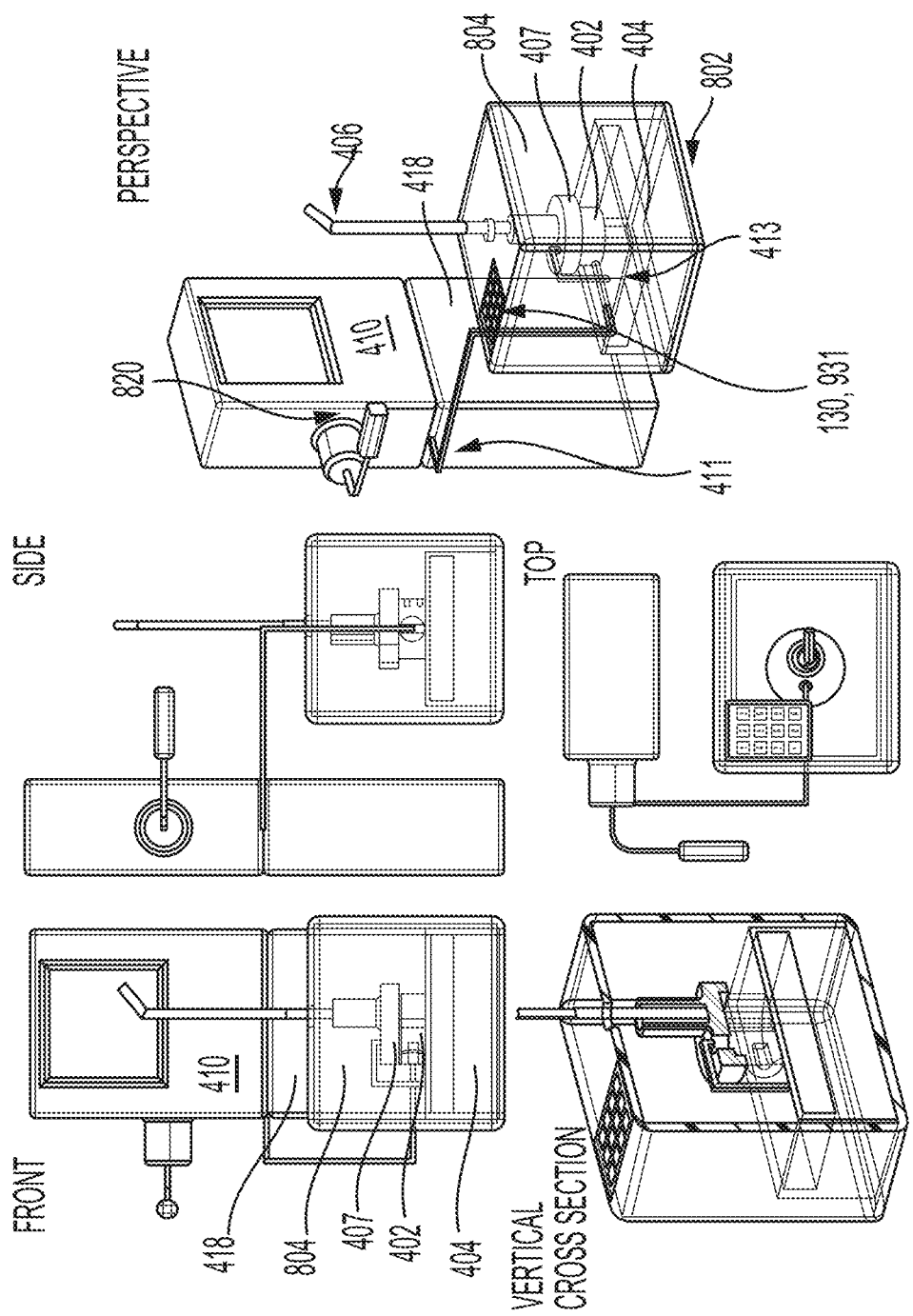
FIG. 11 is a schematic of an oral patient-controlled liquid medicine dispenser according to an embodiment of the invention.

Embodiments of the invention can include one or more security features 130 to discourage tampering and/or diversion of medicine and/or the device. Exemplary security features 130 include a locking device (e.g., require a key or passcode to open the device and/or dispense medicine), a security digital keypad 931, a fingerprint reader 933, a radio frequency identification (RFID) reader 431, a facial recognition system, and/or location tracking device 433 (e.g., using GPS, far-field communications, Lo-ra, dumb chips, satellite communications, and/or network connectivity such as Wi-Fi or cellular networks). For example, in some embodiments, as best illustrated in FIGS. 9 and 11, the security feature 130 includes a digital keypad 931, a fingerprint reader 933, and/or facial recognition. In some embodiments, the patient is required to enter identifying information into the security feature 130 before medication will be dispensed (i.e., a delivery security feature 132) and/or before the medication can be consumed (i.e., a consumption security feature 134). In addition to reducing or eliminating access by unauthorized users, the security feature 130 provides a record of patient medication requests. Additionally or alternatively, in some embodiments, as best illustrated in FIGS. 4 and 5, one or more RFID tags 431 and/or location tracking devices 433 are embedded in the system (e.g., the sealed outer receptacle, the medication reservoir). The embedded RFID tag(s) 431 and/or location tracking devices 433, when present, provide identification and/or tracking of the device.

Figure 12:
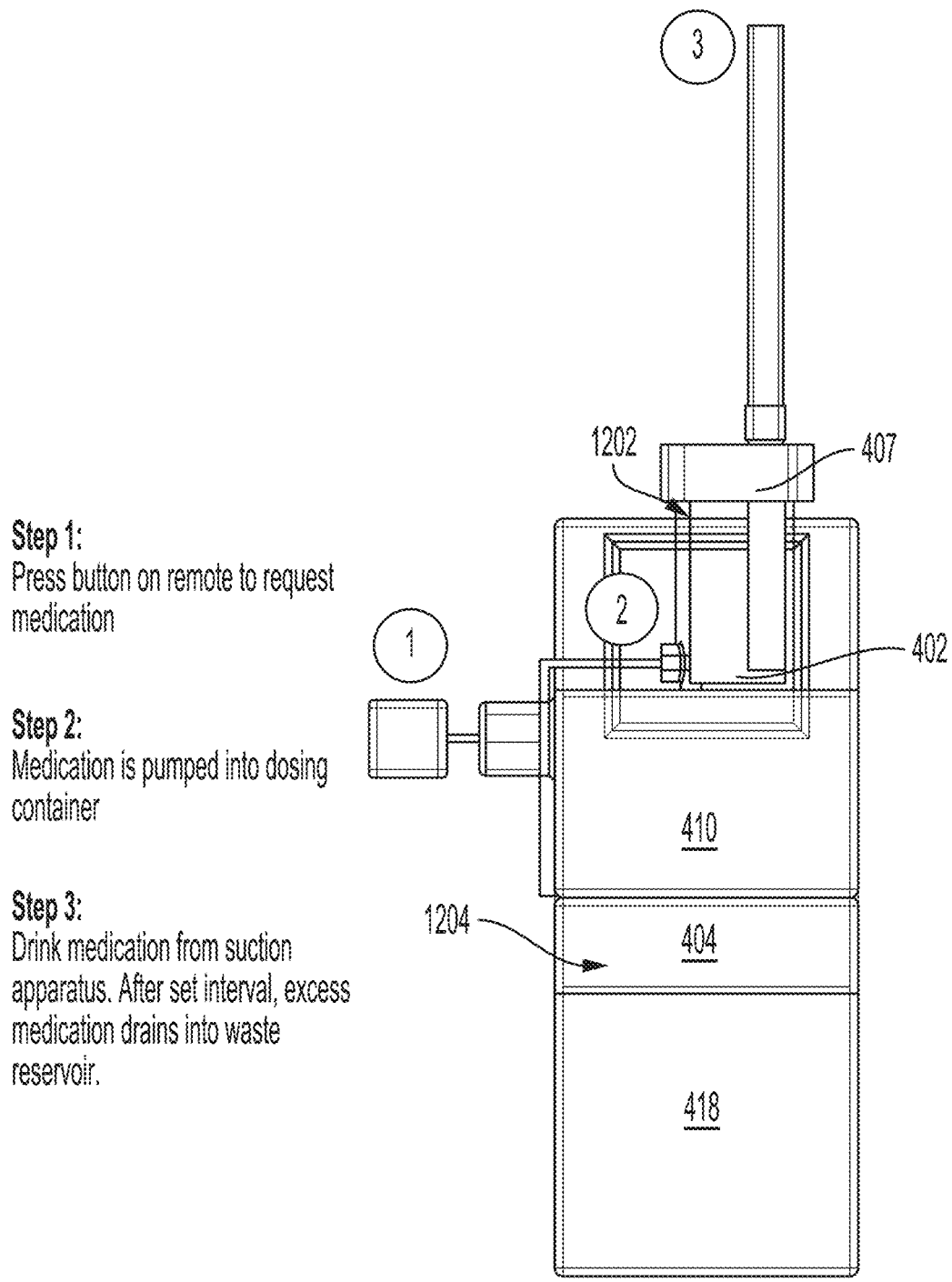
FIG. 12 is a schematic of an oral patient-controlled liquid medicine dispenser according to an embodiment of the invention.

In some embodiments, the security features 130 permit arrangement of the dosing container 402 outside of the sealable waste receptacle 404 and/or without an outer container. For example, in some embodiments, as illustrated in FIG. 12, the dosing receptacle 402 forms a medicine container 1202, which is coupled to a separate waste reservoir 1204 without an outer receptacle. In such embodiments, the medicine container 1202 may include a lid with one or more of the security features 130. The one or more security features 130 prevent unauthorized opening of the medicine container 1202 and/or can trigger release of any fluid in the medicine container 1202 to the waste reservoir 1204 when attempted unauthorized access is detected.

Other security features 130 include, but are not limited to, an alarm, automatic wasting of medication, or any other feature to reduce or eliminate unauthorized access to medication. For example, in some embodiments, the system includes an anti-tampering alarm arranged and disposed to detect attempted tampering with the medication and/or medication flow path from the pump to the medication container. In some embodiments, an electronic timer is configured to waste medication at a set time after being dispensed into the dosing container 402. For example, the system may include an electronic timing valve that automatically wastes any medication in the dosing container 402 after a set duration, such as 30 minutes, to prevent misuse and diversion.

As will be appreciated by those skilled in the art, although various security features are discussed herein with respect to certain embodiments, the disclosure is not so limited and any security feature or combination of security features may be included with any embodiment disclosed herein. For example, any of the embodiments disclosed herein may include a dual security feature, such as, but not limited to, a key pad, finger print reader, and/or facial recognition. Additionally or alternatively, any of the embodiments disclosed herein may include an RFID tag and/or location tracking device.

Electronics

In some embodiments, the system includes one or more electronic communication elements 530 (FIG. 5). In such embodiments, the electronic communication elements 530 are configured to record data from the system, survey the patient, and/or facilitate remote communication with the system. For example, in some embodiments, the electronic communication elements 530 may record data relating to a patient's consumption of medication (e.g., medication dispensed and medication wasted), the frequency of dosing requests, the location of the system (e.g., through GPS location), patient pain levels with each dose request, patient complications with medical recovery (i.e., increase in pain, nausea, vomiting, diarrhea, fever, chills, seats), and/or any other information relating to the system. Additionally or alternatively, the electronic communication elements 530 may survey a patient regarding their pain (e.g., overall, with each dose request), recovery (e.g., improvement, concerns, new symptoms), and/or reported outcome metrics. The data recorded by the electronic communication elements 530 may also be communicated, in real-time or at a later time, to a remote location, such as a smart watch, smart phone, small portable device (e.g., those used in DEXCOM), electronic medical record (e.g., kept by a health care institute and/or accessible by a patient), database (e.g., state or national level), or other remote location. In such embodiments, the data is communicated securely and/or in compliance with any/all relevant regulations (e.g., in a Health Insurance Portability and Accountability Act (HIPAA) sensitive manner). Any such recording and communication of the data may be automatic (i.e., without human input), real-time, scheduled, controlled by human input (e.g., prompted, only collected when requested), or a combination thereof.

Figure 13:
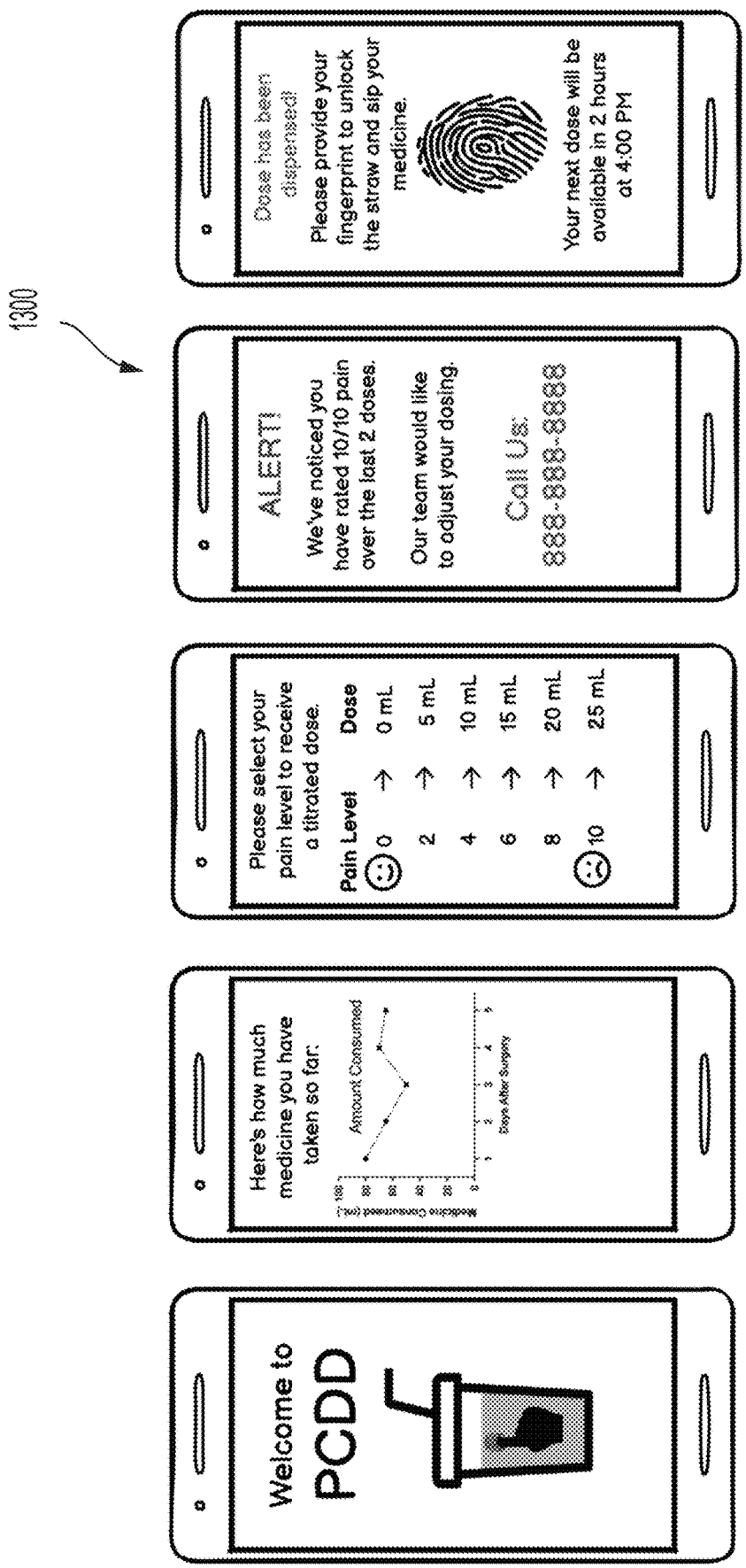
FIG. 13 is an image illustrating an electronic application for use in connection with the system.

Referring to FIG. 13, in some embodiments, the system includes an electronic application 1300. The electronic application 1300 may be executed on any suitable electronic device, such as, but not limited to, a smart watch, phone, or laptop. In some embodiments, the electronic application 1300 displays information about the system, medication, and/or dispensing thereof. In some embodiments, the electronic application is configured to receive user input, such as, but not limited to, pain levels with each dose request, complications with medical recovery (e.g., increase in pain, nausea, vomiting, diarrhea, fever, chills, sweats). Additionally or alternatively, in some embodiments, the electronic application 1300 communicates with the system to dispense medication (within prescribed limits) or otherwise facilitate action in the system.

Suitable electronic communication elements 530 include, but are not limited to, smart chips, near field communication chips, dumb chips, far field, cellular, satellite, or a combination thereof. In some embodiments, the system or device includes a software system to facilitate the recording and/or communication of data by the electronic communication elements 530. Although illustrated in FIG. 5 as being attached to the waste receptacle 404, as will be appreciated by those skilled in the art, the electronic communication elements 530 are not so limited and may be incorporated into and/or secured to any portion of the system. For example, in some embodiments, the system includes electronic communication elements incorporated into the scale 802 and/or the security digital keypad 931.

The recording and communication of data by the electronic communication elements 530 facilitates improved in-patient and remote monitoring. For example, information regarding how much medicine has been consumed and wasted, how frequently patients are requesting medication, and/or pain scores may be recorded in real-time and instantly uploaded to a cloud server, with the data being readily viewable by patients and their healthcare providers at any time. This improved monitoring and documentation may also prevent diversion of the medication by others (e.g., non-patient individuals, health care workers), as any such diversion would be readily detectable in view of the automatic documentation. In some embodiments, the recording and/or communication of data provided herein may relate to controlled substances, such as, but not limited to, opioids, providing accurate, remote documentation of post-discharge consumption thereof. This data may also be communicated to institutional, state, and/or national entities to facilitate the creation of databases and/or to provide data for better patient safety and care. Additionally or alternatively, in some embodiments, the recording and communication of data facilitates remote adjustment of dose and frequency, permitting the provision of such changes to a patient at home after discharge. Accordingly, in some embodiments, the recording and communication of data by the electronic communication elements 530 can provide a real-time tracking database with accurate documentation of all medications consumed, including opioids, and can be instantly linked to institutional, state, and national level databases such as the CDC or medical software such as Epic.

In some embodiments, a PCA pump or an elastomeric pump is configured to pump medication at a specific continuous rate. In such embodiments, the medication flows to a valve, controlled by a security feature, which when open, allows medication to flow into the dosing container 402. If the security feature grants permission to the patient, a valve will open for a specified time, and the continuous flow from the PCA pump or the elastomeric pump permits a specific amount of medication to flow into the dosing container 402. When the valve is closed, although there is continuous positive fluid pressure against the valve, no medication is able to flow into the dosing container. Based on the continuous flow rate, the medical provider can control the amount of medication allowed into the dosing container by controlling the length of time the valve remains open, as well as the number of intervals the valve can be activated each hour.

In some embodiments, the system is configured to calculate and/or record the total amount of volume in the sealed waste receptacle. For example, in some embodiments, at the end of treatment, any extra medication in the medication reservoir is pumped out of the medication reservoir into the sealed waste receptacle. Following the pumping of the extra medication from the medication reservoir to the waste receptacle, the device provides a measurement of the total amount of volume in the waste container, including, but not limited to, any excess medication in the medication reservoir and any medication that was dispensed to the dosing container but not consumed by the patient. In some embodiments, the total amount of volume in the waste receptacle is recorded in the medical record (e.g., by a nurse or automatically by the device), along with a unique encrypted alphanumeric code that embeds the final volume in the waste container. This code allows the pharmacy or authorized healthcare provider to decipher the code and ensure that all medication was wasted and not diverted.

Advantages

Embodiments of the invention provide a number of technical, medical, and economic advantages for patients, the healthcare system, and society.

Patients receive as needed oral medication quickly and safely, are empowered, and have improved patient satisfaction, lower pain scores, and less overall opioid consumption. Additionally, the dosing for each patient may be personalized, providing and/or increasing the ability to be opioid sparing. Furthermore, in contrast to pills, which only come in certain sizes, the liquid dosing can be customized. This customized dosing reduces or eliminates overdosing of patients, particularly geriatric patients.

The healthcare system can avoid or minimize the use of intravenous (IV) patient-controlled pump, require less nursing, realize a lower post-discharge burden on clinics, emergency departments (EDs), and hospitals (e.g., due to readmissions), realize shorter lengths of stay and lower hospitalization cost due to multiple contributors, such as better pain control and fewer side effects, bypassing the need for intravenous patient-controlled pump and subsequent transition to oral medication, realize faster recovery and improved surgical outcomes, and utilize embodiments of the invention as a differentiator to attract patients.

Societal impacts on the opioid pandemic include less medication diversion (illegal transfer of medication to another person). Moreover, embodiments of the invention can facilitate the future of independent, patient-controlled pain management (e.g., in contrast to the current need for patients to visit a methadone clinic regularly in order to receive their dose of methadone, a controlled substance with overdose potential). Overall, less opioid will be used for patients post-surgery. Less active opioid remains in the community. Prescription opioids can be stored securely in liquid format and in a locked box.

Embodiments of the invention can be disposable post-discharge, while current patient-controlled pumps are non-disposable (e.g., due to significant cost) and used only in the hospital. Liquid medication is directly administered to the patient's mouth, reducing the potential for drug diversion. Medication can be securely stored in a locked box. Medication can be delivered via a special one-way locked suction apparatus with anti-theft and anti-spill safety features. Excess medication can be automatically deactivated, potentially by using chemicals like activated charcoal, adding a bitterant, and using a solidifier. In addition to controlled substances, most liquid oral pain medications available on the market today can be administered with embodiments of the invention.

Prophetic Exemplary Uses
Prophetic Exemplary Medicines

Embodiments of the invention can be used with most liquid-format medications, including controlled substances such as opioids and benzodiazepines. Commercially available oral opioids (such as methadone, oxymorphone, hydromorphone, tramadol, codeine, oxycodone, hydrocodone, and morphine) have both tablet format (typically used in adults) and liquid format for pediatric patients and adult patients who have difficulty swallowing pills.

Prophetic Beachhead Population:

Exemplary users of embodiments of the invention include peri-operative patients who will need opioids for pain control and can tolerate oral opioids or other analgesics as needed in the delivery format, specifically with surgeries that require 12 hours or more of post-op inpatient length of stay during which IV patient-controlled pump medication is administered. Exemplary specialties include orthopedics, spine, trauma, general surgery, GI, urology, neurosurgery, OB/GYN, surgical oncology, ENT, chronic pain management, palliative care, and the like.

Prophetic Exemplary Use Case

A 40-year-old female is scheduled for a major spine surgery including T5-S1 laminectomy and fusion. It is anticipated that her postoperative pain control will be challenging and she will need a higher dose of opioids than opioid native patients. Thus, a patient-controlled pump would be ideal in the immediate postoperative period as her pain and opioid needs evolve. Typically, she would receive an intravenous patient-controlled pump, then transition to oral pills (the transition typically takes a day). With our device, we prescribe the patient to receive 5, 10, or 15 mg oxycodone every 3 hours as needed with mild (1-3/10), or moderate (4-6/10) or severe (7-10/10) pain. For the first day after the surgery, the patient self-administers 60 mg oxycodone, the second day 50 mg, and the third day 40 mg. Her self-reported acceptable level of pain is 4/10, and her pain scores never go higher than 6, with 7-10 being severe pain. She reports satisfaction for pain control and confidence in her care. She participates in physical therapy first day after surgery, and is discharged home one day earlier with a 7-day prescription of 5, 10, or 15 mg oxycodone every 3 hours as needed with mild (1-3/10), moderate (4-6/10), or severe (7-10/10) pain, the maximum daily dose of oxycodone being 30 mg. When she no longer needs the opioids, she presses the "deactivation" button on the pump. All leftover medication is pumped from the reservoir to the waste container, deactivated, and solidified. She can then dispose the whole device into a regular household waste container.

The patient never needs to call any healthcare worker for pain medications while in the hospital and at home. She is also reassured by the security features of the patient-controlled pump. More specifically, since the medication is dispensed only when requested via a locked pump and special security locked suction apparatus, she does not have to worry about successfully or unsuccessfully hiding pills from her husband, who has a substance-abuse history. Additionally, she does not need to worry if her 9-year-old son may accidentally drink the oxycodone pain medication while she is recovering from the surgery, as the code key pad and/or finger print and facial recognition reader prevent her son from accessing the medication.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

What is claimed is:

1. A patient-controlled oral liquid-medicine dispenser and deactivation system comprising:
a dosing container having:
a defined volumetric capacity; and
a spillway adapted and configured to allow fluid in excess of the defined volumetric capacity to flow out of the dosing container;
a sealed and tamperproof waste receptacle fluidly coupled to the dosing container, the waste receptacle adapted and configured to capture and prevent diversion of liquid medicine dispensed in excess of the defined volumetric capacity of the dosing container; and
a suction apparatus extending between a lower region of the dosing container and outside of the dosing container.

2. The patient-controlled oral liquid-medicine dispenser and deactivation system of claim 1, wherein the sealed waste receptacle further comprises a neutralizing agent adapted and configured to prevent diversion of liquid medicine by one or more selected from the group consisting of: deactivation, solidification, and bittering.

3. The patient-controlled oral liquid-medicine dispenser and deactivation system of claim 1, wherein the suction apparatus is detachable.

4. The patient-controlled oral liquid-medicine dispenser and deactivation system of claim 1, wherein one or more of the suction apparatus and the dosing container are adapted and configured such that the liquid medicine cannot be delivered from the suction apparatus without suction.

5. The patient-controlled oral liquid-medicine dispenser and deactivation system any one of claim 1, wherein the sealed waste receptacle surrounds the dosing container.

6. The patient-controlled oral liquid-medicine dispenser and deactivation system of claim 5, wherein the sealed waste receptacle and dosing container include an optically transparent or translucent window allowing a user to view the contents of the dosing container, but otherwise obscuring the contents of the sealed waste receptacle.

7. The patient-controlled oral liquid-medicine dispenser and deactivation system of claim 1, wherein the system is configured to waste excess medication in the dosing container.

8. The patient-controlled oral liquid-medicine dispenser and deactivation system of claim 7, further comprising a pump arranged and disposed to pump the excess medication from the dosing container to the sealed waste receptacle after patient use.

9. The patient-controlled oral liquid-medicine dispenser and deactivation system of claim 1, further comprising a medication measurement device arranged and disposed to measure at least one of an amount of medication consumed by a patient and an amount of medication wasted.

10. The patient-controlled oral liquid-medicine dispenser and deactivation system of claim 9, wherein the medication measurement device is selected from the group consisting of a graduated cylinder, a scale, a flow meter, and combinations thereof.

11. The patient-controlled oral liquid-medicine dispenser and deactivation system of claim 1, further comprising at least one electronic communication element arranged and disposed to record data and electronically communicate the recorded data to a remote location.

12. The patient-controlled oral liquid-medicine dispenser and deactivation system of claim 11, wherein the electronic communication element is selected from the group consisting of smart chips, near field communication chips, and a combination thereof.

13. The patient-controlled oral liquid-medicine dispenser and deactivation system of claim 1, further comprising an apparatus for filling the dosing container with a preset volume of a solution containing a liquid medication, the apparatus comprising:
  at least one medication reservoir;
  a pump for delivering the preset volume of the solution to the dosing container, the pump having an inlet and an outlet, and the pump being adapted and configured for fluidic coupling to the at least one medication reservoir;
  a first delivery conduit having a first end and a second end, the first end being coupled to an outlet of the at least one medication reservoir and the second end being coupled to the inlet of the pump; and
  a second delivery conduit having a first end and a second end, the first end being connected to the outlet of the pump, the second end being connected to the dosing container.

14. The patient-controlled oral liquid-medicine dispenser and deactivation system of claim 13, wherein the pump is at least one of re-programmable, adjustable, password-protected, and lockable.

15. The patient-controlled oral liquid-medicine dispenser and deactivation system of claim 13, further comprising at least one security feature configured to prevent dispensing of the solution from the at least one medication reservoir to the dosing container without verification.

16. The patient-controlled oral liquid-medicine dispenser and deactivation system of claim 15, wherein the at least one security feature is selected from the group consisting of a locking device, a security digital keypad, a fingerprint reader, a radio frequency identification (RFID) reader, a facial recognition system, a location tracking device, and combinations thereof.

17. The patient-controlled oral liquid-medicine dispenser and deactivation system of claim 16, wherein the at least one security feature includes a security digital keypad and a fingerprint reader.

18. The patient-controlled oral liquid-medicine dispenser and deactivation system of claim 13, wherein the at least one medication reservoir is removable, refillable, and replaceable by an authorized health care provider based on a physician's prescription.

19. The patient-controlled oral liquid-medicine dispenser and deactivation system of claim 1, wherein the suction apparatus comprises two components.

20. The patient-controlled oral liquid-medicine dispenser and deactivation system of claim 13, wherein the pump is a programmable or adjustable patient-controlled pump.

21. The patient-controlled oral liquid-medicine dispenser and deactivation system of claim 1, wherein the system includes at least one handle.

22. The patient-controlled oral liquid-medicine dispenser and deactivation system of claim 13, wherein the liquid medicine is an opioid or a non-opioid.

23. A method for filling a dosing container with a preset volume of a solution containing a liquid medicine, the method comprising:
  pumping the preset volume of the solution into the dosing container using the patient-controlled oral liquid-medicine dispenser and deactivation system of claim 13;
  wherein the dosing container overflows when the pumped volume exceeds the defined volumetric capacity of the dosing container.

24. The method of claim 23, wherein medication overflow from the dosing container is deactivated in the sealed and tamperproof waste receptacle.

25. The method of claim 24, wherein the deactivated medication is disposable as regular waste.

26. The method of claim 23, wherein the medication cannot be consumed from the dosing container while the medication is being pumped to the dosing container.

27. A method for administering a preset volume of a solution containing a liquid medicine to a subject in need thereof, the method comprising:
  pumping the preset volume of the solution into the dosing container using the patient-controlled oral liquid-medicine dispenser and deactivation system of claim 13; and
  providing the suction apparatus to said patient;
  wherein the patient ingests the preset volume of the solution containing the liquid medicine from the dosing container through the suction apparatus; and
  wherein the dosing container overflows when the preset volume exceeds the defined volumetric capacity of the dosing container.

28. The method of claim 27, wherein the liquid medicine cannot be delivered from the suction apparatus without suction.

29. The method of claim 27, further comprising providing a sliding scale function.

30. The method of claim 27, further comprising:
  tracking the amount of medication consumed by the patient over a period of time; and
  documenting the amount of medication consumed in the patient's medical record.

\* \* \* \* \*